(12) United States Patent
He et al.

(10) Patent No.: US 11,517,289 B2
(45) Date of Patent: Dec. 6, 2022

(54) METHOD AND APPARATUS FOR ACQUIRING MOTION INFORMATION

(71) Applicant: WUXI HISKY MEDICAL TECHNOLOGIES CO., LTD., Wuxi (CN)

(72) Inventors: Qiong He, Wuxi (CN); Jinhua Shao, Wuxi (CN); Jin Sun, Wuxi (CN); Houli Duan, Wuxi (CN); Qiang Wang, Wuxi (CN)

(73) Assignee: WUXI HISKY MEDICAL TECHNOLOGIES CO., LTD., Wuxi (CN)

( * ) Notice: Subject to any disclaimer, the term of this patent is extended or adjusted under 35 U.S.C. 154(b) by 47 days.

(21) Appl. No.: 16/689,022

(22) Filed: Nov. 19, 2019

(65) Prior Publication Data
US 2020/0100769 A1 Apr. 2, 2020

Related U.S. Application Data

(63) Continuation of application No. PCT/CN2018/088406, filed on May 25, 2018.

(30) Foreign Application Priority Data

Jul. 21, 2017 (CN) .......................... 201710649554.8

(51) Int. Cl.
*A61B 8/08* (2006.01)
*A61B 5/00* (2006.01)
*G06F 17/11* (2006.01)

(52) U.S. Cl.
CPC .......... *A61B 8/5223* (2013.01); *A61B 5/0051* (2013.01); *A61B 8/5207* (2013.01); *G06F 17/11* (2013.01)

(58) Field of Classification Search
CPC ... A61B 8/5223; A61B 8/5207; A61B 5/0051; G06F 17/11
See application file for complete search history.

(56) References Cited

U.S. PATENT DOCUMENTS

| 5,099,848 A | 3/1992 | Parker et al. |
| 5,810,731 A | 9/1998 | Sarvazyan |

(Continued)

FOREIGN PATENT DOCUMENTS

| CN | 101034004 A | 9/2007 |
| CN | 102641137 A | 8/2012 |

(Continued)

OTHER PUBLICATIONS

The International Search Report of corresponding International application No. PCT/CN2018/088406, dated Aug. 8, 2018.

(Continued)

*Primary Examiner* — Jason M Ip
(74) *Attorney, Agent, or Firm* — J.C. Patents

(57) ABSTRACT

The present disclosure discloses a method and an apparatus for acquiring motion information. A frequency domain transformation is performed on a detection signal of a vibration propagating in a medium to obtain a frequency domain signal, then a signal that is outside of a defined vibration velocity range is removed from the frequency domain signal, that is, only a vibration signal is retained, and then a position-time diagram is obtained along a defined vibration propagation direction. It is not necessary to perform motion estimation on propagation of the vibration by a complicated calculation, and it is only necessary to determine the presence or absence of the vibration by processing in the frequency domain, and then the position-time diagram is obtained, which is a highly efficient method for acquiring motion information.

10 Claims, 7 Drawing Sheets

(56) References Cited

U.S. PATENT DOCUMENTS

| | | |
|---|---|---|
| 7,464,583 B1 | 12/2008 | Kowalewski |
| 8,211,019 B2 | 7/2012 | Sumi |
| 8,469,891 B2 | 6/2013 | Maleke |
| 9,554,771 B2 | 1/2017 | Shao |
| 2004/0034304 A1* | 2/2004 | Sumi .................... A61B 5/0051 600/439 |
| 2012/0215101 A1 | 8/2012 | Maleke |
| 2014/0018679 A1 | 1/2014 | Chen |
| 2014/0343424 A1 | 11/2014 | Konotagou |
| 2015/0080730 A1 | 3/2015 | Kanayama |
| 2015/0094579 A1 | 4/2015 | Fan |
| 2016/0051195 A1 | 2/2016 | Pang |
| 2016/0302769 A1 | 10/2016 | Labyed |
| 2017/0042511 A1 | 2/2017 | Labyed |
| 2017/0143213 A1 | 5/2017 | Nadkarni |

FOREIGN PATENT DOCUMENTS

| | | |
|---|---|---|
| CN | 103054552 A | 4/2013 |
| CN | 103995053 A | 8/2014 |
| CN | 104302233 A | 1/2015 |
| CN | 104640506 A | 5/2015 |
| CN | 105455851 A | 4/2016 |
| CN | 106037796 A | 10/2016 |
| CN | 106419961 A | 2/2017 |
| CN | 107440740 A | 12/2017 |
| CN | 107505232 A | 12/2017 |
| CN | 107505233 A | 12/2017 |
| JP | 5753633 B2 | 7/2015 |
| KR | 1020110086120 A | 5/2010 |
| KR | 101307526 B1 | 9/2013 |
| KR | 101620507 B1 | 5/2016 |
| WO | WO1999023940 A1 | 5/1999 |
| WO | WO2010012092 A1 | 2/2010 |
| WO | 2014/055410 A1 | 4/2014 |
| WO | WO2014136502 | 3/2017 |

OTHER PUBLICATIONS

The Chinese First Examination Report of corresponding Chinese application No. 201710649554.8, dated Mar. 1, 2019.
The Chinese Allowance Report of corresponding Chinese application No. 201710649554.8, dated Aug. 1, 2019.
The first Office Action of BR application No. 1120190252649.
The first Office Action of JP application No. 2020-503053.
The first Office Action of AU application No. 2018301989.
The Notice of Allowance of CN application No. 201710649552.9.
The first Office Action of corresponding India application IN202047007340.
"Time domain formulation of pulse-Doppler ultrasound and blood velocity estimation by cross correlation", Ultrasonic Imaging, Academic Press. Inc., vol. 8 Jan. 1, 1986, pp. 73-85.
NPL1: "Ultrasonic imaging of the internal vibration of soft tissue under forced vibration", The Journal of the Acoustical Society of America 84, S139 (1988); doi: 10.1121/1.2025806.
NPL2: "An Apparatus for Producing Mechanical Step Pulses for Biorheologic Studies", IEEE Transactions on Biomedical Engineering, May 1972, pp. 251-252.

* cited by examiner

METHOD AND APPARATUS FOR ACQUIRING MOTION INFORMATION

CROSS-REFERENCE TO RELATED APPLICATIONS

This application is a continuation of International Application No. PCT/CN2018/088406, filed on May 25, 2018, which claims priority to Chinese Patent Application No. 201710649554.8, filed on Jul. 21, 2017, both of which are hereby incorporated by reference in their entireties.

TECHNICAL FIELD

The disclosure relates to the field of measurement technology, and in particular to a method and an apparatus for acquiring motion information.

BACKGROUND

When a medium is excited by vibration, propagation characteristics of the vibration in the medium are related to a viscoelasticity of the medium. By measuring the propagation characteristics of the vibration, the viscoelasticity of the medium can be quantified. To obtain the propagation characteristics of the vibration, it is necessary to obtain motion information of the vibration by using a detection signal for the vibration.

The above principle has been applied to a number of technical fields at present. Taking medical detection as an example, when detecting an organ or tissue such as liver, thyroid and muscle, a lesion can be positioned by quantifying the viscoelasticity of the medium.

Therefore, how to efficiently obtain the motion information of the vibration propagating in the medium is a problem that needs to be solved.

SUMMARY

Embodiments of the present disclosure provide a method and an apparatus for acquiring motion information. For a purpose of a basic understanding of some aspects of the disclosed embodiments, a brief summary is given below. This summary is not intended to provide general statements, nor to identify key/critical constituent elements or to delineate the scope of protection of these embodiments. Its sole purpose is to present some concepts in a simple form as a preface to the detailed explanation that follows.

According to a first aspect of the embodiments of the present disclosure, a method for acquiring motion information is provided, including:

performing a frequency domain transformation on a detection signal of a vibration propagating in a medium to obtain a frequency domain signal;

removing a signal that is outside of a defined vibration velocity range from the frequency domain signal to obtain a processed signal; and obtaining a position-time diagram of the vibration using the processed signal.

According to the method, as a first optional embodiment, the removing a signal that is outside of a defined vibration velocity range from the frequency domain signal to obtain a processed signal includes:

performing a filtration or a feature value selection on the frequency domain signal to obtain the processed signal, where a parameter of the filtration is related to the defined vibration velocity range, and the feature value selection is related to the defined vibration velocity range.

According to the method, as a second optional embodiment, the obtaining a position-time diagram of the vibration using the processed signal includes:

obtaining the position-time diagram of the vibration using the processed signal according to a defined vibration propagation direction.

According to the method, as a third optional embodiment, the method further includes:

performing an image segmentation on the position-time diagram;

extracting an image feature;

performing a linear fitting using the image feature to obtain a slope of a slope line of the position-time diagram; and calculating a viscoelasticity parameter of the medium according to the slope.

According to the method, as a fourth optional embodiment, the method further includes:

performing an angle projection on the position-time diagram along each angle within a preset angle range and determining a slope of the position-time diagram corresponding to an angle at which signal energy is maximum; and obtaining the viscoelasticity parameter of the medium according to the slope.

According to the fourth embodiment, as a fifth optional embodiment, the performing an angle projection on the position-time diagram along each angle within a preset angle range and determining a slope of the position-time diagram corresponding to an angle at which signal energy is maximum includes:

performing an integral calculation on the position-time diagram along each angle within the preset angle range;

determining an angle corresponding to a largest integral value as a slope angle of a slope line of the position-time diagram; and determine the slope of the slope line using the slope angle.

According to a second aspect of the embodiments of the present disclosure, an apparatus for acquiring motion information is provided, including:

a first processing module, configured to perform a frequency domain transformation on a detection signal of a vibration propagating in a medium to obtain a frequency domain signal;

a second processing module, configured to remove a signal that is outside of a defined vibration velocity range from the frequency domain signal to obtain a processed signal; and an acquiring module, configured to obtain a position-time diagram of the vibration using the processed signal.

According to the apparatus, as a first optional embodiment, the second processing module performs a filtration or a feature value selection on the frequency domain signal to obtain the processed signal, where a parameter of the filtration is related to the defined vibration velocity range, and the feature value selection is related to the defined vibration velocity range.

According to the apparatus, as a second optional embodiment, the acquiring module obtains the position-time diagram of the vibration using the processed signal according to a defined vibration propagation direction.

According to the apparatus, as a third optional embodiment, the apparatus further includes:

a viscoelasticity quantifying module, configured to:

perform an image segmentation on the position-time diagram, extract an image feature and perform a linear fitting using the image feature to obtain a slope of a slope line of the position-time diagram; and calculate a viscoelasticity parameter of the medium according to the slope.

According to the apparatus, as a fourth optional embodiment, the apparatus further includes:

a viscoelasticity quantifying module, configured to: perform an angle projection on the position-time diagram along each angle within a preset angle range and determine a slope of the position-time diagram corresponding to an angle at which signal energy is maximum; and obtain a viscoelasticity parameter of the medium according to the slope.

According to the fourth embodiment, as a fifth optional embodiment, the viscoelasticity quantifying module includes:

a calculating sub-module, configured to perform an integral calculation on the position-time diagram along each angle within the preset angle range;

a determining sub-module, configured to: determine an angle corresponding to a largest integral value calculated by the calculating sub-module as a slope angle of a slope line of the position-time diagram; and determine the slope of the slope line using the slope angle; and a quantifying sub-module, configured to obtain the viscoelasticity parameter of the medium according to the slope.

According to a third aspect of embodiments of the present disclosure, a device for acquiring motion information is provided, including:

a memory, storing execution instructions;

a processor, configured to read the execution instructions to accomplish the following operations:

performing a frequency domain transformation on a detection signal of a vibration propagating in a medium to obtain a frequency domain signal;

removing a signal that is outside of a defined vibration velocity range from the frequency domain signal to obtain a processed signal; and obtaining a position-time diagram of the vibration using the processed signal.

The technical solution provided by the embodiments of the present disclosure may have the following advantageous effects:

Frequency domain transformation is performed on a detection signal of a vibration propagating in a medium to obtain a frequency domain signal, then a signal that is outside of a defined vibration velocity range is removed from the frequency domain signal, that is, only a vibration signal is retained, and then a position-time diagram of the vibration is obtained. Thus, it is not necessary to perform motion estimation on propagation of the vibration by a complicated calculation, and it is only necessary to determine the presence or absence of the vibration by processing in the frequency domain, and then the position-time diagram is obtained, which is a highly efficient method for acquiring motion information.

It is to be understood that both the foregoing general description and the following detailed description are exemplary and explanatory only and are not to limit the disclosure.

BRIEF DESCRIPTION OF THE DRAWINGS

The accompanying drawings, which are incorporated in and constitute a part of this specification, illustrate embodiments consistent with the disclosure and, together with the specification, serve to explain the principle of the disclosure.

DETAILED DESCRIPTION OF THE EMBODIMENTS

The following descriptions and drawings sufficiently illustrate specific embodiments of the disclosure so that they can be implemented by those skilled in the art. The embodiments represent only possible variations. Individual components and functions are optional unless explicitly specified otherwise, and the order of the operations may vary. Portions and features of some embodiments may be included in or substituted for portions and features of other embodiments. The scope of the embodiments of the present disclosure includes the full scope of the claims, and all available equivalents of the claims. Herein, each embodiment may be represented individually or collectively by the term "disclosure". This is merely for convenience, and if more than one disclosure is in fact disclosed, it is not intended to automatically limit the scope of the application to any single disclosure or inventive concept. Herein, relation terms such as "first" and "second" are used merely to distinguish an entity or operation from another entity or operation, without requiring or implying that any substantial relation or order exists between these entities or operations. Moreover, the terms "include", "comprise" or any other variations thereof are intended to cover nonexclusive inclusions, so that a process, a method or a device including a series of elements not only includes the elements, but also includes other elements that are not set forth specifically. Various embodiments herein are described in a progressive manner, and each embodiment focuses on the differences from other embodiments. The same or similar parts between the embodiments may be referred to each other. For the structures, products etc. disclosed in the embodiments, since they correspond to the parts disclosed in the method embodiments, only a relatively simple description is given, and the related parts can be referred to the description of the method parts.

Figure 1:
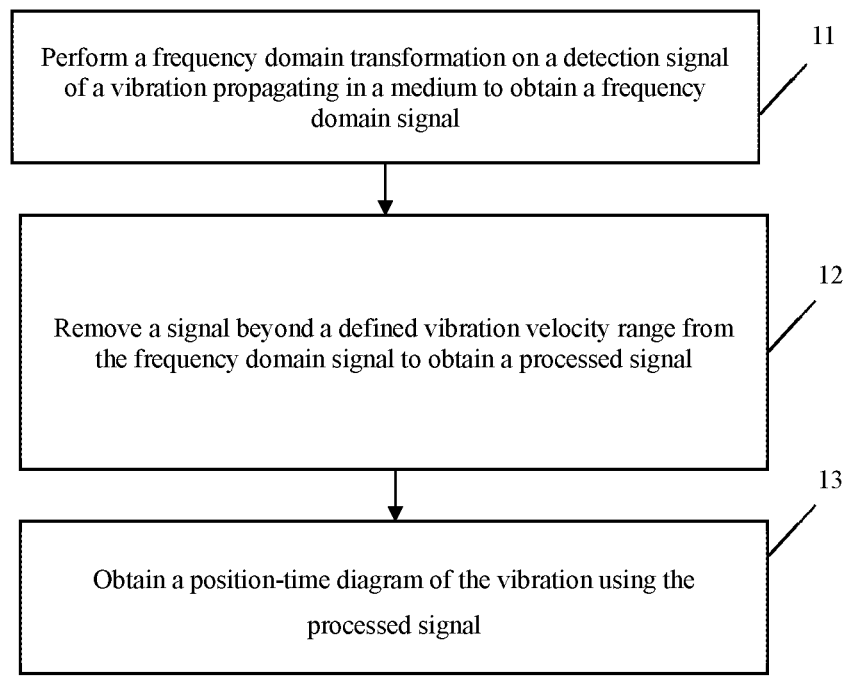
FIG. 1 is a flow chart showing a method for acquiring motion information according to an exemplary embodiment.

FIG. 1 is a flow chart showing a method for acquiring motion information according to an exemplary embodiment. As shown in FIG. 1, the method includes the following steps.

In step 11, perform a frequency domain transformation on a detection signal of a vibration propagating in a medium to obtain a frequency domain signal.

In step 12, remove a signal that is outside of a defined vibration velocity range from the frequency domain signal to obtain a processed signal.

In step 13, obtain a position-time diagram of the vibration using the processed signal.

After a medium is stimulated by a vibration, the vibration propagates in the medium, with its wavefront reaching different positions at different times along a propagation direction. Such a correspondence between the positions and the times is motion information of the vibration, i.e. position-time diagram of the vibration. At present, conventional method for acquiring the motion information utilizes that phase de-correlation of the detection signal of the vibration occurs when the medium vibrates, according to the characteristic of this phase de-correlation, a position-time diagram of the vibration can be obtained by an algorithm such as cross-correlation, self-correlation or optical flow, and any method based on block matching can be selected as the algorithm. In this conventional method for acquiring the motion information, it is needed to perform a motion estimate on propagation of the vibration using information such as displacement and strain of the medium before the position-time diagram of the vibration is obtained.

In the present exemplary embodiment, by using the characteristic that the detection signal includes information of the vibration which generates Doppler effect, the detection signal is subjected to frequency domain transformation in an imaging time dimension to obtain a frequency domain signal, from which a signal that is outside of a defined vibration velocity range is removed, that is, a signal that is relatively static or has a low vibration velocity is removed. Then the position-time diagram of the vibration is obtained. It can be seen that the method for acquiring the motion information in the present exemplary embodiment does not require a complicated calculation. Instead, by performing processing in the frequency domain, the position-time diagram that is not characterized by displacement or strain can be obtained. This method does not need to perform motion estimation on propagation of the vibration, and it is only necessary to determine the presence or absence of the vibration to obtain the position-time diagram, which is a highly efficient method for acquiring the motion information.

In an exemplary embodiment, in step 11, the frequency domain transformation may be performed in various ways, such as Fourier transform or singular value decomposition.

In an exemplary embodiment, in step 12, the removing a signal that is outside of a defined vibration velocity range from the frequency domain signal to obtain a processed signal may be implemented by performing a filtration or a feature value selection on the frequency domain signal. Taking that the filtration is used to implement the above removal operation as an example, in order to retain only the signal whose vibration velocity is within the defined vibration velocity range, a filtration parameter of a filter can be set by considering the sampling rate of the signal in space and time and combining with a defined vibration velocity range, e.g., 0.1 m/s to 30 m/s. Thus, the signal outside of the defined vibration velocity range can be removed from the frequency domain signal based on the filtration. When the feature value selection is used to implement the removal operation, selection of the feature value can also be set in relation to the defined vibration velocity range, thereby removing the signal outside of the defined vibration velocity range from the frequency domain signal. By step 12, only the signal of the vibration can be retained, improving the accuracy of subsequent formation of the position-time diagram.

In an exemplary embodiment, after performing a vibration excitation on the medium by mechanical vibration, acoustic radiation force or other means that can generate vibration, the medium generates a vibration, and the vibration propagates in the medium. Since the above-mentioned vibration has a limited propagation velocity in the medium, dynamic imaging of the medium can be performed using the detection signal. The detection wave may be a light wave, an ultrasonic wave, or the like. The above dynamic imaging may be one-dimensional imaging, two-dimensional imaging, three-dimensional imaging or the like. Regardless of the imaging mode, the position-time diagram of the vibration can be obtained using the processed signal after the above-mentioned removal operation and according to the defined vibration propagation direction. The defined vibration propagation direction is an actual propagation direction of the vibration when the vibration propagates in only one propagation direction, and it is a selected one of the propagation directions when the vibration propagates in a plurality of propagation directions. For example, when the medium is a uniform sheet, after performing a vibration excitation on the medium, the vibration will propagate along an extending direction of the sheet, and at this time the defined vibration propagation direction is the actual propagation direction of the vibration. For another example, when the medium is in a three-dimensional irregular shape, the wavefront of the vibration propagation is in a three-dimensional shape, for example, an ellipsoid shape, then the position-time diagrams obtained along different vibration propagation directions are different, and at this time the defined vibration propagation direction is a selected one of propagation direction of interest. The above-mentioned propagation direction of interest is determined according to the direction to be actually measured, and may be, for example, at least one of: the direction in which the vibration propagates fastest, the direction in which the vibration propagates slowest, and the direction in which the vibration propagation velocity is within a certain range.

Figure 2:
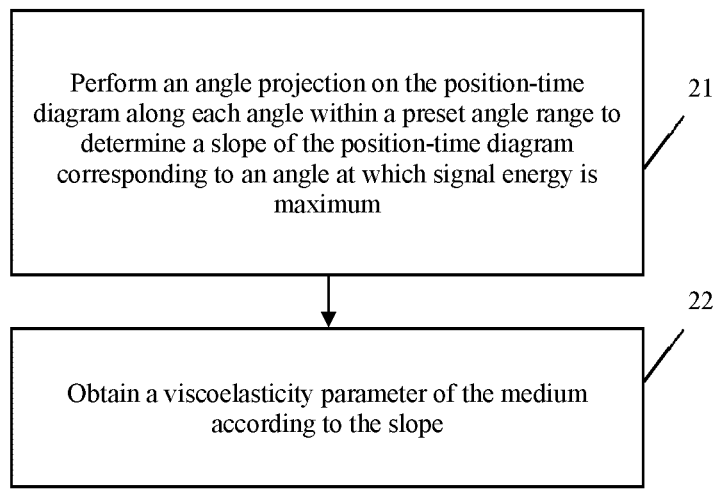
FIG. 2 is a flow chart showing a method for quantifying viscoelasticity of a medium according to an exemplary embodiment.

In an exemplary embodiment, the method shown in FIG. 1 may further include a step for quantifying the viscoelasticity of the medium. FIG. 2 is a flow chart showing a method for quantifying the viscoelasticity of the medium according to an exemplary embodiment, which is implemented based on the flow shown in FIG. 1, and includes the following steps.

In step 21, perform an angle projection on the position-time diagram along each angle within a preset angle range to determine a slope of the position-time diagram corresponding to an angle at which signal energy is maximum.

The preset angle range refers to an angle range selected for the angle projection according to an actual situation. As an optional implementation, the preset angle range may be 360 degrees, and at this time a full-angle angle projection is needed. As another optional implementation, the angle range for the angle projection may be selected according to the characteristic of the position-time diagram obtained. In the position-time diagram obtained in step 11, the horizontal axis indicates the time and the vertical axis indicates the position. If the vibration propagates only from the starting point of the vibration excitation to the distance, then when the velocity of the vibration propagation is infinite, a straight line approximately parallel to the vertical axis will be seen on the position-time diagram. Instead, when the velocity of the vibration propagation is infinitely small, a straight line approximately parallel to the horizontal axis will be seen on the position-time diagram. At this time, a preset angle range of 90 degrees can meet the demand, without a need to perform a full-angle projection, thereby improving the efficiency of quantifying the viscoelasticity of the medium. If the vibration may also propagate in an opposite direction in addition to propagating from the starting point of the vibration excitation to the distance, then the preset angle range may be 180 degrees. As for the actual starting point and ending point of the preset angle range, when the Cartesian coordinate system remains unchanged, it is related to the starting point of 0 degree and the counterclockwise or clockwise rotation direction, and can be selected as needed as long as the preset angle range is guaranteed.

The each angle refers to each of angles at which angle projections are performed within the preset angle range. Selection of a specific angle is determined according to time precision requirement and calculation speed requirement. The higher the time precision requirement, the higher the precision requirement of angle selection, and the higher the calculation speed requirement, the lower the precision requirement of the angle selection. For example, it may be selected from the range of 0.01 degree to 1 degree.

The angle projection refers to recognition or extraction of image features for a defined angle to determine the angle at which the signal energy is maximum.

In step 22, obtain a viscoelasticity parameter of the medium according to the slope.

The viscoelasticity parameter includes at least one of: a viscosity parameter and an elasticity parameter.

The slope of the position-time diagram is determined by the distance propagated by the vibration per unit time, i.e., velocity of the vibration propagating in the medium. In a homogeneous medium, the velocity of vibration propagation is related to the viscoelasticity of the medium. After the slope of the position-time diagram is obtained, the viscoelasticity parameter of the medium can be quantitatively calculated. Therefore, how to obtain the above slope efficiently and accurately is the key to quantifying the viscoelasticity of the medium. The present exemplary embodiment uses the angle projection to determine the angle at which the signal energy is maximum, that is, the slope of the position-time diagram is obtained, since the angle at which the signal energy is maximum corresponds to the slope of the position-time diagram. This method does not need to select a peak, a trough, or a certain phase of the vibration from the position-time diagram as a feature point to calculate the slope of the position-time diagram, and this method is not subject to noise interference, has a small amount of calculation, which is an efficient and accurate method for quantifying the viscoelasticity of the medium.

Figure 3:
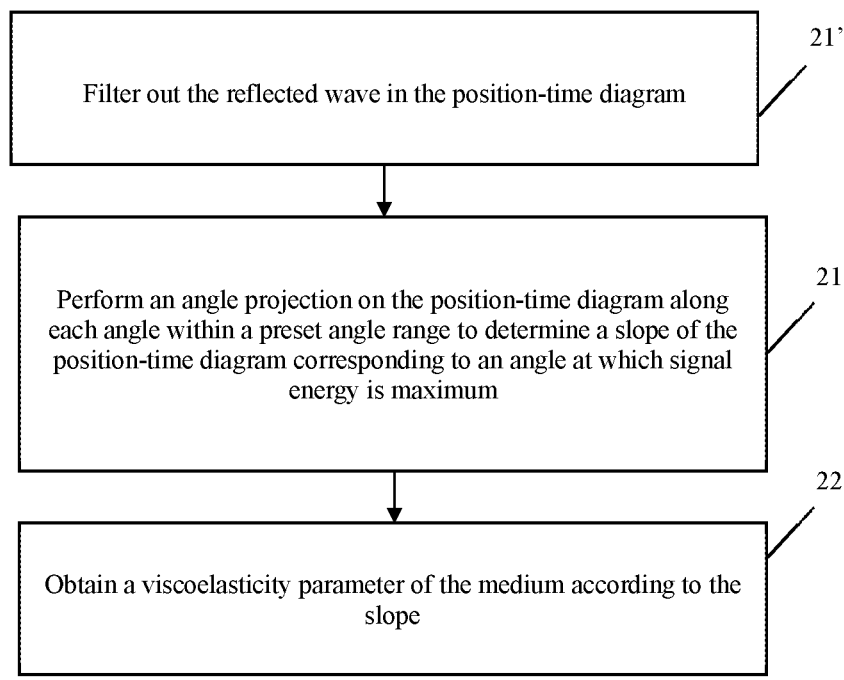
FIG. 3 is a flow chart showing a method for quantifying viscoelasticity of a medium according to an exemplary embodiment.

When the vibration propagates in the medium and encounters an edge or foreign matter of the medium, a reflected wave is generated. To improve the accuracy of the subsequent processing, as shown in FIG. 3, a step 21', i.e., filtering out the reflected wave in the position-time diagram may further be included before the angle projection is performed. There are many ways to filter, and directional filtering is one of the implementations.

As an optional implementation, determining the angle at which the signal energy is maximum via the angle projection to obtain the slope of the position-time diagram may be achieved by an integral calculation. For example, integral calculation along each angle within the preset angle range is performed on the position-time diagram. The energy is concentrated when an integration angle is consistent with the vibration propagation direction, and the integral value obtained at this moment is the largest, so the angle at which the integral value is the largest is the slope angle of the slope line of the position-time diagram. According to the obtained slope angle in combination with the position and time information, the slope of the slope line of the position-time diagram can be obtained. The above integral calculation is also referred to as Radon transform.

As another optional embodiment, determining the angle at which the signal energy is maximum via the angle projection to obtain the slope of the position-time diagram may also be achieved by calculating a gray-level co-occurrence matrix. Since an image texture feature can be obtained by calculating the gray-level co-occurrence matrix, and the image texture feature can reflect the magnitude of the signal energy, the gray-level co-occurrence matrix can be used to obtain the information of the angle at which the signal energy is maximum. Based on the above principle, determining the angle at which the signal energy is maximum via the angle projection to obtain the slope of the position-time diagram may be achieved by calculating a gray-level co-occurrence matrix. For example, for the position-time diagram, the gray-level co-occurrence matrix is firstly calculated along each angle within the preset angle range. Then, the gray-level co-occurrence matrix is used to obtain the image texture feature of each angle. Next, using the image texture feature, the angle at which the signal energy is maximum is determined as the slope angle of the slope line of the position-time diagram. Finally, the slope of the slope line is determined using the slope angle.

Figure 4:
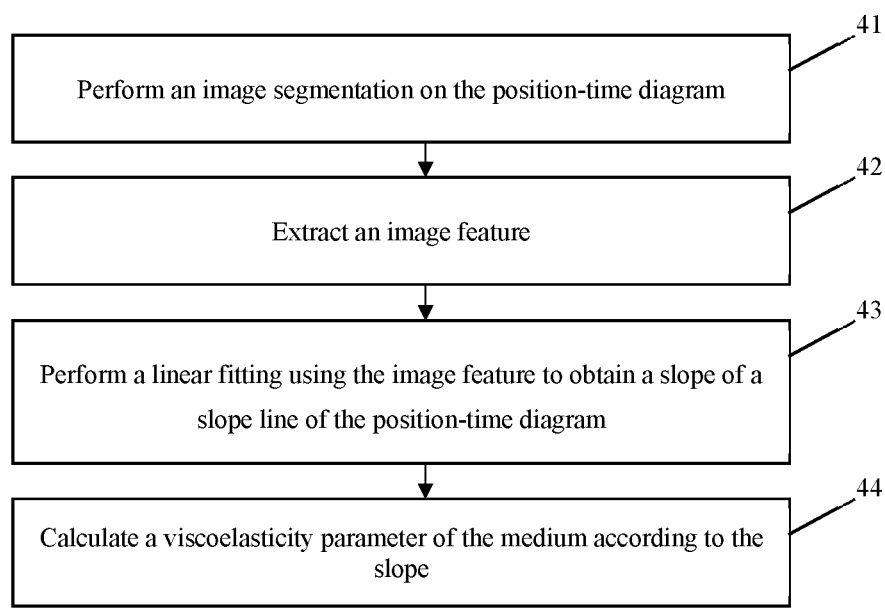
FIG. 4 is a flow chart showing a method for quantifying viscoelasticity of a medium according to an exemplary embodiment.

In an exemplary embodiment, the method shown in FIG. 1 may further include a step of medium viscoelasticity quantifying. FIG. 4 is a flow chart showing a method for quantifying the viscoelasticity of the medium according to an exemplary embodiment, which is implemented based on the flow shown in FIG. 1, and includes the following steps.

In step 41, perform an image segmentation on the position-time diagram.

In step 42, extract an image feature.

The image feature may be at least one of a central axis, a peak, a trough, and a zero crossing point. The above-mentioned central axis refers to the skeleton of the pattern on the position-time diagram, and the zero-crossing point refers to the point with a maximum slope value or the point with a maximum value of second derivative. The image feature extracted contains information of the vibration.

In step 43, perform a linear fitting using the image feature to obtain a slope of a slope line of the position-time diagram.

In step 44, calculate a viscoelasticity parameter of the medium according to the slope.

In the foregoing two exemplary embodiments for quantifying the viscoelasticity of the medium, according to the mechanical principle, the viscoelasticity of the medium determines the propagation velocity of the vibration in the medium. Therefore, by obtaining the slope of the position-time diagram, the propagation velocity of the vibration in the medium can be known. And then, according to the mechanical principle, the viscoelasticity parameter of the medium can be quantitatively derived. Here, the viscoelasticity parameter may include shear modulus, Young's modulus, viscous modulus, shear viscoelasticity, shear viscosity, mechanical resistance, mechanical relaxation time or anisotropy, etc.

Optionally, when the linear fitting is employed to quantify the viscoelasticity of the medium, the reflected wave in the position-time diagram may be filtered out first to achieve a more accurate quantitative effect.

The application of the method for acquiring motion information in the embodiments of the present disclosure is given below in a specific application scenario.

When non-invasive viscoelasticity detection is performed on a viscoelastic medium such as a human liver, it is necessary to quantify the viscoelasticity of the medium, and the motion information needs to be obtained before the quantification. An excitation device and an imaging device are included in the detection device, where the excitation device performs a vibration excitation to the medium to be detected, and the imaging device uses an ultrasonic wave to image the medium after the vibration excitation. When the vibration propagates in the medium, the wavefront reaches different positions at different times along the propagation direction, forming the position-time diagram. The above wavefront may be one of a peak, a trough, or a certain phase of the vibration.

Figure 5:
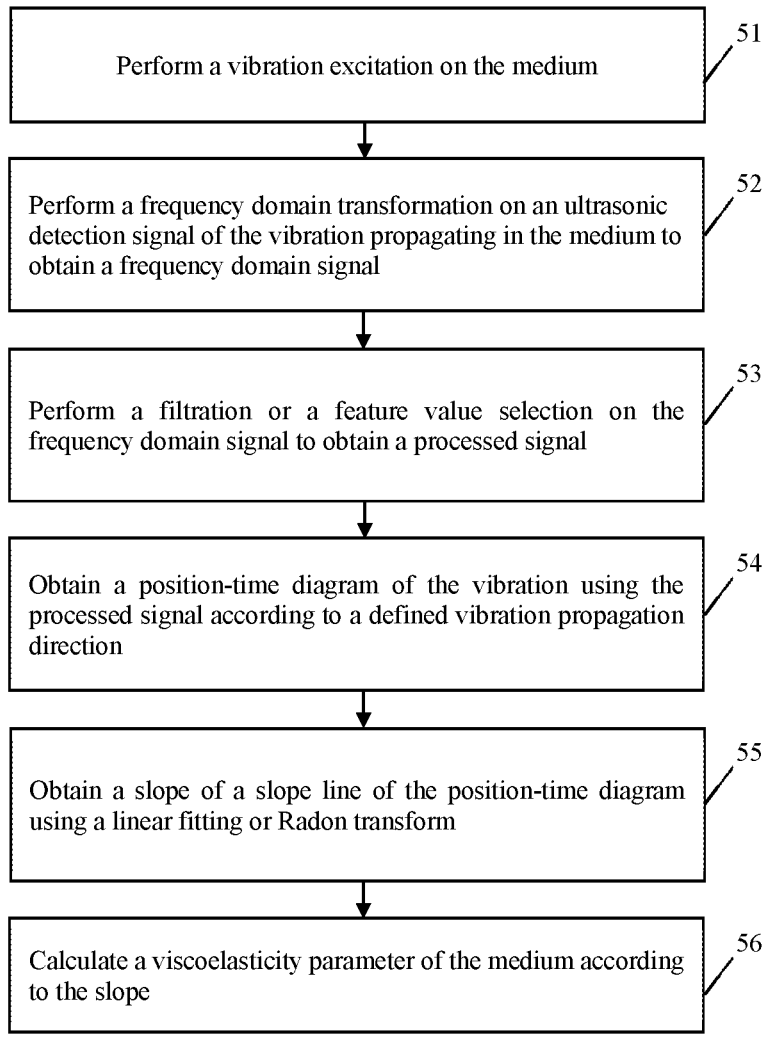
FIG. 5 is a flow chart showing a method for acquiring motion information according to an exemplary embodiment.

As shown in FIG. 5, the method for acquiring motion information in this specific application scenario may include the following steps.

In step 51, perform a vibration excitation on the medium.

In step 52, perform a frequency domain transformation on an ultrasonic detection signal of the vibration propagating in the medium to obtain a frequency domain signal.

In step 53, perform a filtration or a feature value selection on the frequency domain signal to obtain a processed signal.

In step 54, obtain a position-time diagram of the vibration using the processed signal according to a defined vibration propagation direction.

In step 55, obtain a slope of a slope line of the position-time diagram using a linear fitting or Radon transform.

In step 56, calculate a viscoelasticity parameter of the medium according to the slope.

In the various exemplary embodiments of the method for acquiring motion information, for the step of medium viscoelasticity quantifying, when there are at least two defined vibration propagation directions, each defined vibration propagation direction corresponds to one position-time diagram. Then, the viscoelasticity parameter of the medium corresponding to the position-time diagram will be obtained. Combining the obtained at least two sets of viscoelasticity parameters, the viscoelasticity of the medium can be more comprehensively evaluated.

The respective exemplary embodiments of the method for acquiring motion information as described above can be combined according to circumstances, and the combination relationship between the respective exemplary embodiments is not limited herein.

Figure 6:
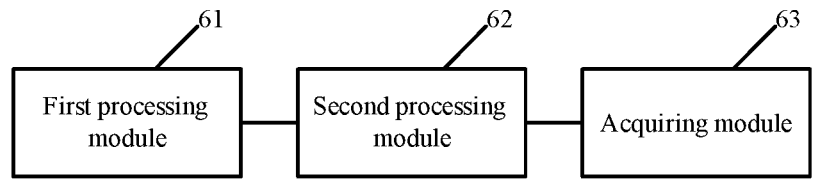
FIG. 6 is a block diagram showing an apparatus for acquiring motion information according to an exemplary embodiment.

FIG. 6 is a block diagram showing an apparatus for acquiring motion information according to an exemplary embodiment. The apparatus may be located in a control host of a detection device for the medium viscoelasticity. For example, in the field of medical detection, the apparatus may be located in a control host of a liver non-invasive detection device. The apparatus may also be located in a cloud, in which case the detected data of the detection device for the medium viscoelasticity needs to be processed in the cloud.

The apparatus shown in FIG. 6 includes a first processing module 61, a second processing module 62, and an acquiring module 63.

The first processing module 61 is configured to perform a frequency domain transformation on a detection signal of a vibration propagating in a medium to obtain a frequency domain signal. The first processing module 61 may use various methods, such as Fourier transform or singular value decomposition, to perform the frequency domain transform.

The second processing module 62 is configured to remove a signal that is outside of a defined vibration velocity range from the frequency domain signal to obtain a processed signal.

The acquiring module 63 is configured to obtain a position-time diagram of the vibration using the processed signal.

In an exemplary embodiment, the second processing module 62 performs a filtration or a feature value selection on the frequency domain signal to obtain the processed signal. The parameter of the filtration is related to the defined vibration velocity range, and the feature value selection is related to the defined vibration velocity range.

In an exemplary embodiment, the acquiring module 63 obtains the position-time diagram of the vibration using the processed signal and according to a defined vibration propagation direction.

Figure 7:
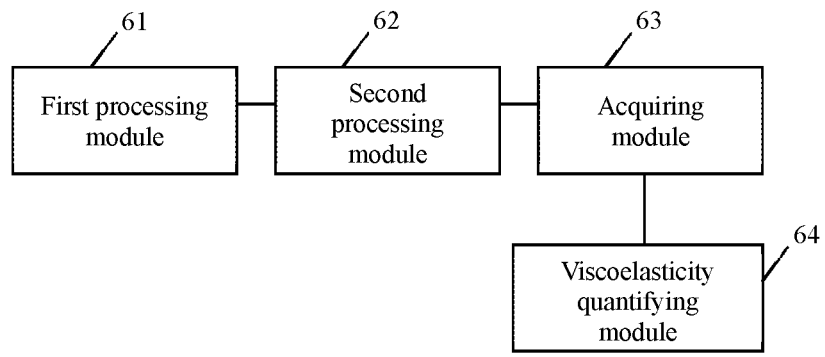
FIG. 7 is a block diagram showing an apparatus for acquiring motion information according to an exemplary embodiment.

In an exemplary embodiment, as shown in FIG. 7, the apparatus shown in FIG. 6 may further include: a viscoelasticity quantifying module 64, which is configured to: perform an image segmentation on the position-time diagram; extract an image feature; perform a linear fitting using the image feature to obtain a slope of a slope line of the position-time diagram; and calculate a viscoelasticity parameter of the medium according to the slope. The term "image feature" here has the same meaning as that described in the previous method.

As another optional implementation, the viscoelasticity quantifying module 64 may also use an angular projection to achieve the same function. The viscoelasticity quantifying module 64 is configured to: perform an angle projection on the position-time diagram along each angle within a preset angle range to determine the slope of the position-time diagram corresponding to an angle at which signal energy is maximum; and obtain the viscoelasticity parameter of the medium according to the slope.

Figure 8:
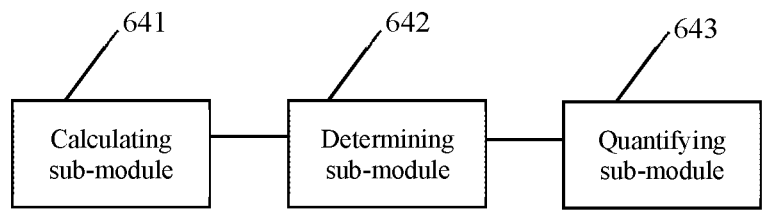
FIG. 8 is a block diagram showing the viscoelasticity quantifying module shown in FIG. 7.

Further, optionally, as shown in FIG. 8, the viscoelasticity quantifying module 64 may include a calculating sub-module 641 and a determining sub-module 642.

The calculating sub-module 641 is configured to perform an integral calculation on the position-time diagram along each angle within the preset angle range.

The determining sub-module 642 is configured to: determine an angle corresponding to a largest integral value, which is calculated by the calculating sub-module 641, as a slope angle of a slope line of the position-time diagram. Using the slope angle, the slope of the slope line is determined.

The quantifying sub-module 643 is configured to obtain the viscoelasticity parameter of the medium according to the slope.

As another optional implementation, the viscoelasticity quantifying module 64 may, in addition to the above integral calculation method, determine the slope by calculating a gray-level co-occurrence matrix. At this time, the calculating sub-module 641 is configured to, for the position-time diagram, calculate the gray-level co-occurrence matrix along each angle within the preset angle range. The determining sub-module 642 is configured to: obtain an image texture feature of each angle; determine, using the image texture feature, the angle at which signal energy is maximum as the slope angle of the slope line of the position-time diagram; and determine the slope of the slope line using the slope angle.

Figure 9:
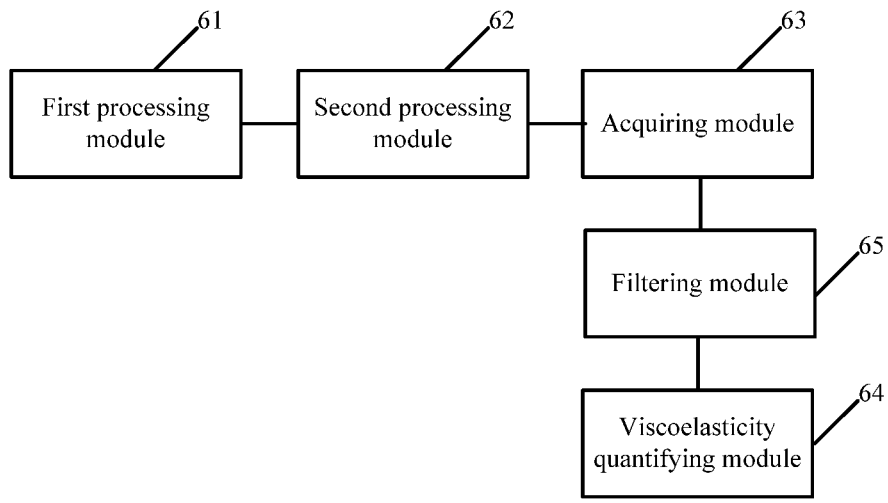
FIG. 9 is a block diagram showing an apparatus for acquiring motion information according to an exemplary embodiment.

Further, optionally, as shown in FIG. 9, the apparatus for acquiring motion information further includes a filtering module 65, which is configured to filter out a reflected wave in the position-time diagram before the viscoelasticity quantifying module 64 performs the angle projection. Of course, when linear fitting is employed to quantify the viscoelasticity of the medium, the filtering module 65 may first filter out the reflected wave in the position-time diagram.

Figure 10:
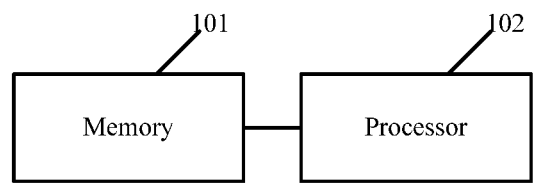
FIG. 10 is a block diagram showing a device for acquiring motion information according to an exemplary embodiment.

FIG. 10 is a block diagram showing a device for acquiring motion information according to an exemplary embodiment. The device may be located in a control host of a detection device for medium viscoelasticity. For example, in the field of medical detection, the device may be located in a control host of a liver non-invasive detection device. The device may also be located in a cloud, in which case the detected data of the detection device for medium viscoelasticity needs to be processed in the cloud.

The device shown in FIG. 10 includes a memory 101 and a processor 102.

The memory 101 stores execution instructions.

The processor 102 is configured to read the execution instructions in the memory 101 and perform some or all of the steps in various exemplary embodiments of the method for acquiring motion information described above. The processor 102 may be implemented by a chip.

If the device for acquiring motion information shown in FIG. 10 is located in the control host of the detection device for medium viscoelasticity, the device may be coupled to an excitation device and an imaging device in the detection device for the medium viscoelasticity by means of a bus, wireless or the like. At this time, the device is provided with an interface and a corresponding communication mechanism to achieve the above coupling.

If the device for acquiring motion information shown in FIG. 10 is located in a cloud, it can communicate with the detection device for the medium viscoelasticity through a network.

It will be appreciated that the present disclosure is not limited to the process and construction that has been described above and illustrated in the accompanying drawings, and that various modifications and changes can be made without departing from the scope of the present disclosure. The scope of the present disclosure is limited only by the appended claims.

What is claimed is:

1. A method for acquiring motion information, wherein the method is not based on a displacement measurement, and the method comprises:
   performing, by an exciting device, a vibration excitation on a medium to be detected to make the medium generate vibration and the vibration propagate in the medium, a wavefront of the vibration reaches different positions at different times along a propagation direction to form motion information of the vibration, the motion information of the vibration is a correspondence between the positions and the times;
   performing, by an imaging device using a detection signal, dynamic imaging for the medium;
   subjecting the detection signal to frequency domain transformation in an imaging time dimension by using the characteristic that the detection signal comprises information of the vibration which generates Doppler effect, to obtain a frequency domain signal;
   removing a signal that is outside of a defined vibration velocity range, from the frequency domain signal to obtain a processed signal; and
   obtaining a position-time diagram of the vibration in a set propagation direction using the processed signal, wherein the position-time diagram represents the motion information of the vibration, wherein a horizontal axis of the position-time diagram indicates time, and a vertical axis of the position-time diagram indicates position of the wavefront of the vibration;
   wherein the removing a signal that is outside of a defined vibration velocity range, from the frequency domain signal to obtain a processed signal comprises:
   performing a filtration or a feature value selection on the frequency domain signal to obtain the processed signal, wherein
   a parameter of the filtration is related to the defined vibration velocity range, and
   the feature value selection is related to the defined vibration velocity range.

2. The method according to claim 1, wherein the obtaining a position-time diagram of the vibration using the processed signal comprises:
   obtaining the position-time diagram of the vibration using the processed signal according to a defined vibration propagation direction.

3. The method according to claim 1, wherein the method further comprises:
   performing an image segmentation on the position-time diagram;
   extracting an image feature;
   performing a linear fitting using the image feature to obtain a slope of a slope line of the position-time diagram; and
   calculating a viscoelasticity parameter of the medium according to the slope.

4. The method according to claim 1, wherein the method further comprises:
   performing an angle projection on the position-time diagram along each angle within a preset angle range and determining a slope of the position-time diagram corresponding to an angle at which signal energy is maximum; and
   obtaining a viscoelasticity parameter of the medium according to the slope.

5. The method according to claim 4, wherein the performing an angle projection along each angle within a preset angle range on the position-time diagram and determining a slope of the position-time diagram corresponding to an angle at which signal energy is maximum comprises:
   performing an integral calculation on the position-time diagram along each angle within the preset angle range;
   determining an angle corresponding to a largest integral value as a slope angle of a slope line of the position-time diagram; and
   determining the slope of the slope line using the slope angle.

6. A device for acquiring motion information, wherein the device is not based on a displacement measurement, and the device comprises:
   a memory, storing execution instructions; and
   a processor, configured to read the execution instructions to accomplish the following operations:
   performing, by an exciting device, a vibration excitation on a medium to be detected to make the medium generate vibration and the vibration propagate in the medium, a wavefront of the vibration reaches different positions at different times along a propagation direction to form motion information of the vibration, the motion information of the vibration is a correspondence between the positions and the times;

performing, by an imaging device using a detection signal, dynamic imaging for the medium;

subjecting the detection signal to frequency domain transformation in an imaging time dimension by using the characteristic that the detection signal comprises information of the vibration which generates Doppler effect, to obtain a frequency domain signal;

removing a signal that is outside of a defined vibration velocity range, from the frequency domain signal to obtain a processed signal; and obtaining a position-time diagram of the vibration in a set propagation direction using the processed signal, wherein the position-time diagram represents the motion information of the vibration, wherein a horizontal axis of the position-time diagram indicates time, and a vertical axis of the position-time diagram indicates position of the wavefront of the vibration;

wherein the processor is configured to read the execution instructions to perform a filtration or a feature value selection on the frequency domain signal to obtain the processed signal, wherein a parameter of the filtration is related to the defined vibration velocity range, and the feature value selection is related to the defined vibration velocity range.

7. The device according to claim 6, wherein the processor is configured to read the execution instructions to obtain the position-time diagram of the vibration using the processed signal according to a defined vibration propagation direction.

8. The device according to claim 6, wherein the processor is further configured to read the execution instructions to:

perform an image segmentation on the position-time diagram, extract an image feature and perform a linear fitting using the image feature to obtain a slope of a slope line of the position-time diagram; and calculate a viscoelasticity parameter of the medium according to the slope.

9. The device according to claim 6, wherein the processor is further configured to read the execution instructions to:

perform an angle projection on the position-time diagram along each angle within a preset angle range and determine a slope of the position-time diagram corresponding to an angle at which signal energy is maximum; and obtain a viscoelasticity parameter of the medium according to the slope.

10. The device according to claim 9, wherein the processor is configured to read the execution instructions to:

perform an integral calculation on the position-time diagram along each angle within the preset angle range;

determine an angle corresponding to a largest integral value as a slope angle of a slope line of the position-time diagram; and determine the slope of the slope line using the slope angle; and obtain the viscoelasticity parameter of the medium according to the slope.

\* \* \* \* \*